United States Patent [19]

Markoll

[11] Patent Number: 5,453,073
[45] Date of Patent: Sep. 26, 1995

[54] APPARATUS FOR TREATMENT OF DISEASED BODY ORGANS WITH MAGNETIC FIELD THERAPY

[76] Inventor: Richard Markoll, 17791 Saxony Ct., Boca Raton, Fla. 33496

[21] Appl. No.: 202,871

[22] Filed: Feb. 28, 1994

Related U.S. Application Data

[60] Continuation of Ser. No. 867,446, Apr. 13, 1992, abandoned, which is a division of Ser. No. 519,410, May 4, 1990, Pat. No. 5,131,904.

[51] Int. Cl.⁶ .................................................... A61N 1/00
[52] U.S. Cl. ................................................ 600/14; 600/15
[58] Field of Search ................ 600/9–15; 607/154–156; 5/511, 601, 624; 269/55, 56, 67–68

[56] References Cited

U.S. PATENT DOCUMENTS

| | | | |
|---|---|---|---|
| 3,915,151 | 10/1975 | Kraus | 600/13 |
| 4,641,633 | 2/1987 | Delgado | 600/13 |
| 4,674,482 | 6/1987 | Waltonen et al. | 128/1.5 |

FOREIGN PATENT DOCUMENTS

| | | |
|---|---|---|
| 0048451 | 3/1982 | European Pat. Off. |
| 0181053 | 5/1986 | European Pat. Off. .......... A61N/1/42 |
| 2353959 | 5/1975 | Germany. |

*Primary Examiner*—Lee S. Cohen
*Assistant Examiner*—John P. Lacyk
*Attorney, Agent, or Firm*—Dallett Hoopes

[57] ABSTRACT

Apparatus for treating organs by applying a magnetic field by means of an annular coil surrounding the organ, the coil being energized by a pure DC voltage having a rectangular wave form pulsing at the rate of 1–30 CPS. The invention also includes an apparatus comprising a body support encompassed by an annular coil energized as above. The coil is mounted on a carriage running on tracks adjacent the body support.

9 Claims, 3 Drawing Sheets

5,453,073

APPARATUS FOR TREATMENT OF DISEASED BODY ORGANS WITH MAGNETIC FIELD THERAPY

This is a continuation of application Ser. No. 07/867,446, filed Apr. 13, 1992 now abandoned which is a divisional of application Ser. No. 07/519,410 filed May 4, 1990 now U.S. Pat. No. 5,131,904.

BACKGROUND OF THE INVENTION

1. Field of the Invention

This invention relates to the treatment of disease including painful, degenerative, injurious, or inflammatory conditions of the human musculoskeletal system or parts thereof, or other body organ systems or parts thereof affected by such conditions. More specifically, this invention relates to the application of a magnetic field to these systems or parts thereof to alter, arrest, or heal those said diseases and conditions, or relieve pain or other uncomfortable or unwanted sensations associated with these named diseases and conditions, and apparatus for delivering such magnetic field for the stated purpose.

2. Description of Related Art including Information Disclosed under §§1.97 to 1.99

It has been recognized in the prior art that the application of a magnetic field to diseased organs can in some way improve the condition. An example is disclosed in the Kraus U.S. Pat. No. 3,915,151 which discloses the idea of imparting a low frequency AC source to a wound toroid into which an ailing limb is inserted. The imparted voltage creates a changing magnetic field. This treatment is coupled in Kraus with a galvanic action by means of plates disposed on either sides of the limb.

A more recent U.S. Pat. No. 4,537,181 to Shaloob et al, discloses treating a patient with a magnetic field created by rotating permanent magnets.

Other patents somewhat of interest to the present invention are U.S. Pat. Nos. 4,233,965 issued Nov. 18, 1980 and 4,758,429 issued Jul. 19, 1988.

SUMMARY OF THE INVENTION

Under the present invention the target organ is subjected to an electromagnetic field driven by a pure DC voltage having an abruptly rising and abruptly deteriorating wave form at the rate of 1–30 pulses per second. The field at the target organ is of low intensity, preferably under 20 gauss, and the field lines are oriented, where the target organ is on an appendage, such that the flux lines travel toward the distal end of the appendage.

The effect of the treatment under the present invention is dramatic as will be demonstrated in examples hereunder. The exact mechanism by which the treatment derives its efficacy is not known but one explanation may be found in the uni-directonal elongated (extended) prolongation and abruptly shortened repolarization theory:

Directing a specific time frequency and wave form, of low amplitude magnetic field (flux) into and onto a target area of living tissue/organ in an almost axial arrangement for an extended specified length of time, allows (causes) the electron (ionic) flow to remain in either a plus or minus state. This action does stimulate the electrical potential. Thus a regeneration (repair) process is initiated by (during) which the cells (tissue/organs) are able to and will (better) more fully perform their intended genetic function(s).

The cells (tissue/organs) may therefore carry out their functions in a more appropriate fashion and healthy physiological intended manner. The healing process, once stimulated, is henceforth maintained by nature of the permanently enhanced positive electron balance and healthy metabolic status.

In amplification of the above theory, I have concluded from a careful review of recent data concerning the intrinsic magnetic field strength of living individuals that all human beings possess measurable amounts of a magnetic field (MF). The data further indicates that most healthy people have a MF which ranges from X to Y gauss. Some human beings have extremely low MF levels: other human beings have extremely high MF levels, i.e. 4 to 5 times (X+Y/2). Based on a correlation between healthy and morbid human beings, I postulate that further investigation should be initiated which might suggest that altered magnetic properties may represent the state of disease, that is, derangement of MF may correlate with disease.

The following specification represents a new approach based on the above theory.

BRIEF DESCRIPTION OF THE DRAWINGS

Other features and objects of the invention will be clear from the following specification including the drawings, all of which disclose a non-limiting form of the invention. In the drawings.

DESCRIPTION OF THE PREFERRED EMBODIMENT

Figure 2:
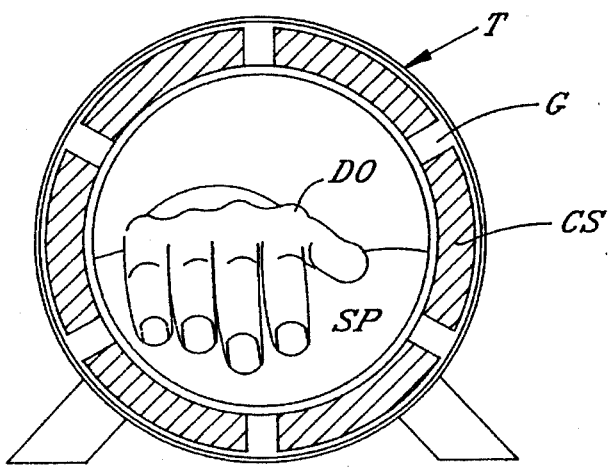
FIG. 2 is a front end view with front of cover removed and showing the coil segments inside the toroid.

Referring to the drawings, the invention involves the creation of an electromagnetic field F. This field is created by energizing a winding in a toroid T such that the field forms a three-dimensional donut in and about the toroid. The toroid T within its case contains a number of coil segments CS spaced by air gaps G as shown in FIG. 2. It is an important characteristic of the invention that the field not be greater than 20 gauss in the area of the diseased organ DO.

Figure 3:
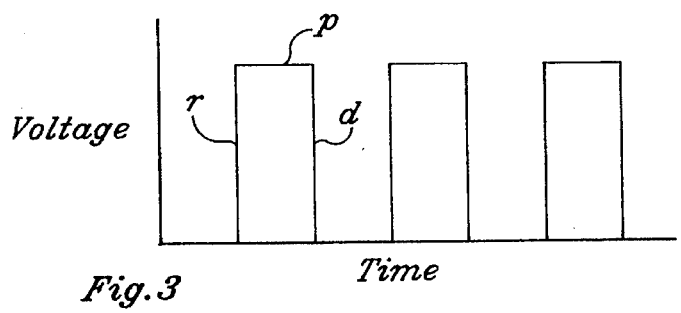
FIG. 3 is a graph showing the voltage flow vs. time as imparted to the toroid air coil to induce the magnetic field under the invention.

After much study, it has been found that it is important that voltage be supplied to the toroid winding in a pattern demonstrated in FIG. 3. The voltage supplied must repeatedly build up steeply, hold, and then deteriorate steeply and so that there are thus created a series of spaced working plateaus p of pure DC current. It is preferred, therefore, that in the duty cycle the wave form of the pure DC voltage involved be virtually of rectangular shape with the abruptly rising r and abruptly falling d sides of the wave form comprising sides of a rectangle. In between two such duty cycles there is an off cycle.

As an additional characteristic, further study has indicated that it is important that the movement of the field along the diseased limb, for instance, be toward its distal end. Thus, for instance, when treating a patient's hand as shown, or knee, as the diseased organ, the magnetic lines of the field F in the area of the organ should move toward the end of the appendage remote from the torso. This is achieved by supplying voltage of proper polarity to the coil leads of the toroid T.

As shown in FIG. 2, the target diseased organ DO is supported to be in position eccentric to the central flux portion of the magnetic field within the toroid. This can be accomplished by a shapeable fiber support pillow SP of cotton or the like which need not completely surround the organ, but should assist its proper positioning. Inside the toroid housing, as stated, are a series of circularly arranged arcuate segments, of wound coil CS. With respect to the size of the toroid, it is important that the distance between the organ and the windings be no greater than about six inches (6").

It has further been found, as a result of much experimentation, that the length of time intervals between the treatment periods and the length of the treatment periods themselves is important. Preferably the length of periods should be no greater than one-half hour and the frequency should be every 24 to 48 hours through the treatment period.

DESCRIPTION OF APPARATUS FOR TREATING ORGANS IN THE TORSO

The invention also has application, aside from treatment of the limbs, to diseased organs on the main part of the body, i.e., the torso. Equipment which has been used for such torso treatment is shown in the drawings, FIGS. 4 through 7.

Figure 4:
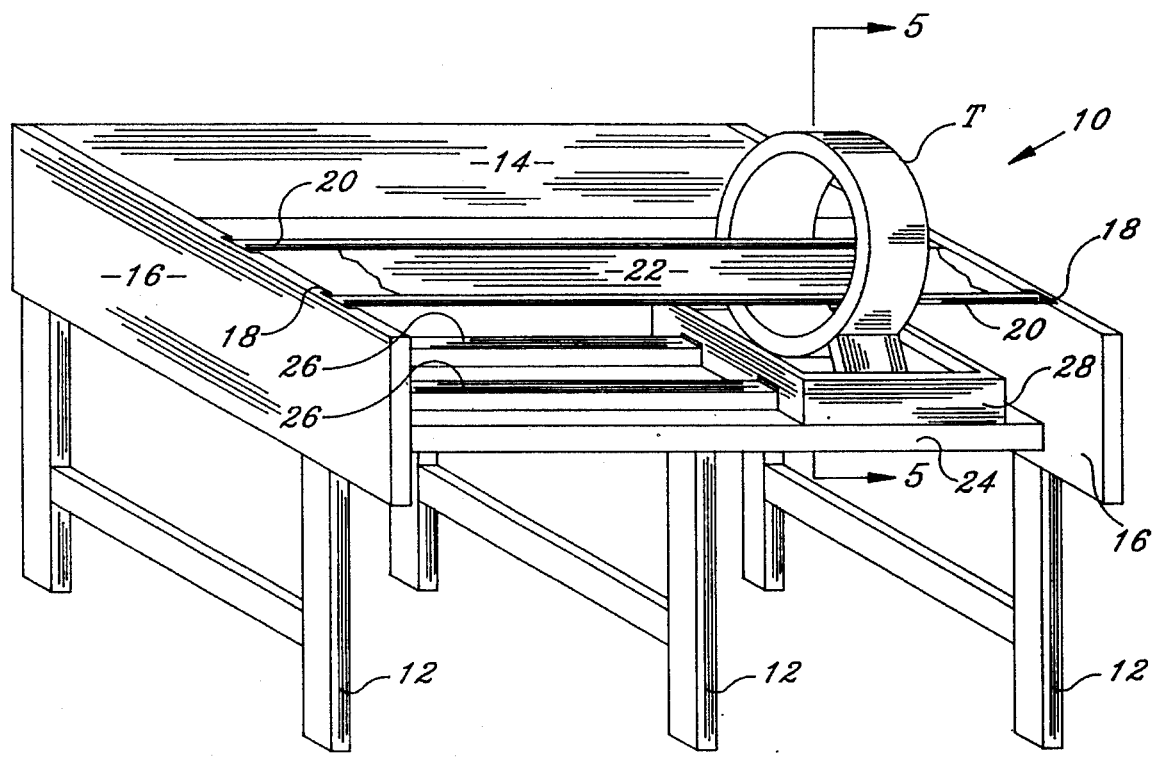
FIG. 4 is a perspective view of a table embodying an apparatus of the invention.
Figure 5:
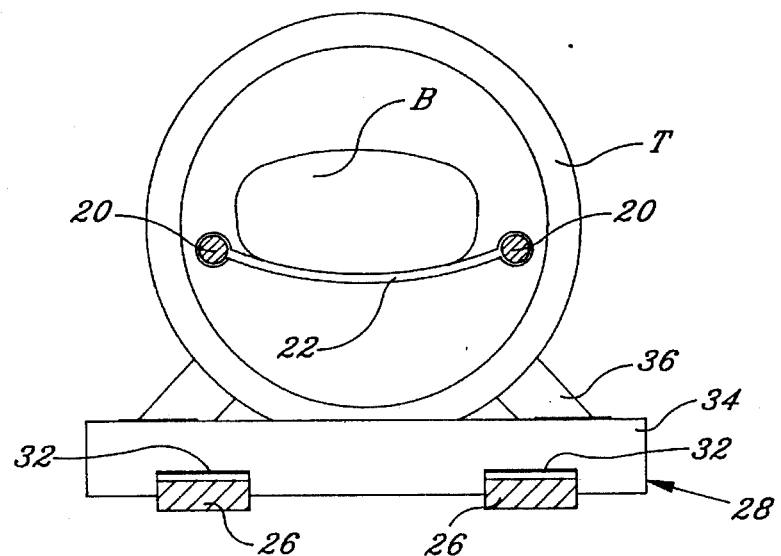
FIG. 5 is an enlarged front end view of the carriage showing the tracks in section.
Figure 6:
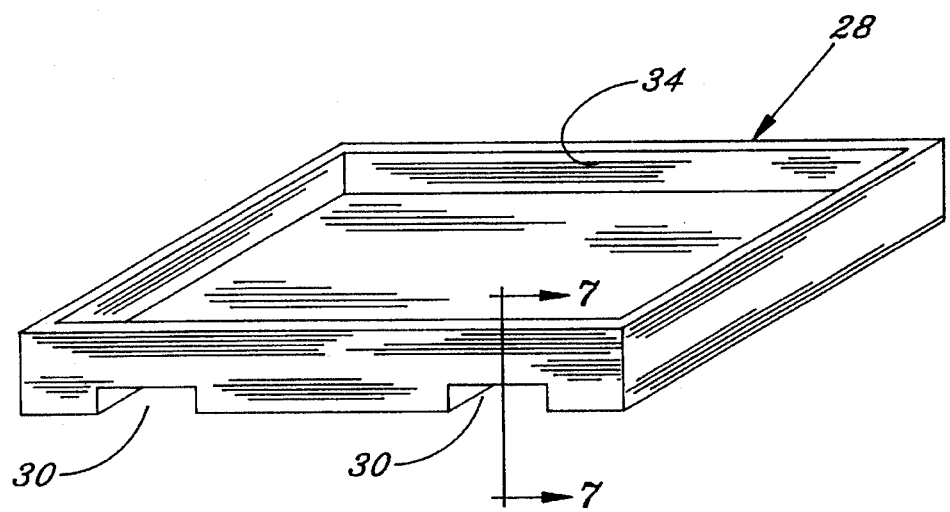
FIG. 6 is an enlarged perspective view of the carriage for supporting the toroid.
Figure 7:
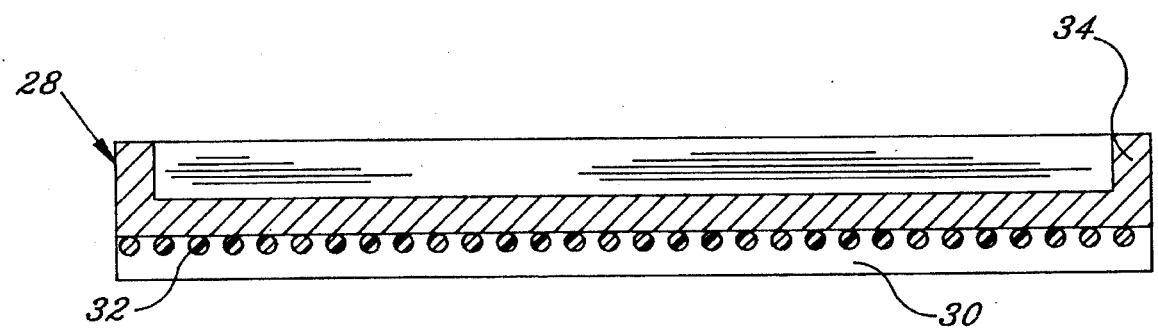
FIG. 7 is a sectional view taken on the line 7—7 of FIG. 6.

FIG. 4 shows an apparatus useful in applying a magnetic field to the main part of the human body, i.e. The torso. It is generally designated 10 and is an all wood table comprising a plurality of support legs 12, a horizontal transitional surface 14 on which the patient may sit and then recline and prepare himself. The support surface 14 is preferably supported on a pair of end boards 16 which are supported by the legs and are notched as at 18 to support rails 20 which has between them a fabric support web 22.

Extending between the side board 16 and horizontally disposed at a level below the surface 14 is a coil support bed 24. Supported on the bed 24 are a pair of spaced parallel tracks 26 which may be in the form of boards having a rectangular cross section. A coil support carriage 28 is provided with a pair of side-by-side upward recesses 30 which fit slideably over the tracks 26.

Figure 1:
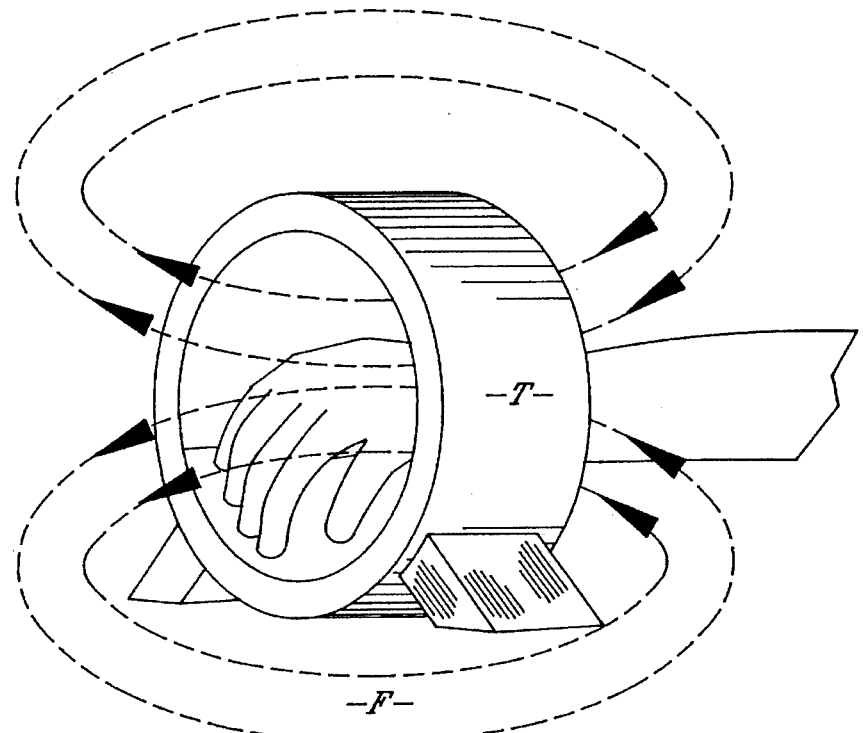
FIG. 1 is a simplified perspective view of a wound toroid energized to develop an electromagnetic field as indicated by flux lines, shown treating a diseased hand.

Anti-friction means, such as plastic rollers 32, are mounted adjacent the upper wall of the recess 30 so that the carriage may easily move along the tracks. Preferably the upper sides of the carriage are formed with a circumferential lip 34. The toroid T, similar to that disclosed in FIGS. 1 and 2, is equipped with downward flaring legs 36 which are received onto the carriage 28 to support the toroid.

In use, the patient reclines on tile surface 14 and then, with the carriage 28 at one end of the tracks 26, the patient rolls onto the fabric support web 22 so that his body B is supported thereby. The carriage then moves along the tracks 26 until the toroid T, encompassing his body, is aligned with the diseased organ. The toroid is then energized for treatment as described above.

I have found that for treatment of the hand a toroid having an opening of 5½" is preferable, an opening of 11" may be useful in treatment of the knee and for a treatment of the entire body, as in FIGS. 4 through 7, an opening of 22" is suitable for most patients.

EXAMPLES

The following examples of treatment show results after indicated procedures, all within the scope of the invention as described above.

Example 1

Patient #1 had severe arthritis of his right knee documented by Magnetic Resonance Imaging which demonstrated significant cartilaginous disease and cystic disease in his knee. He had this problem for more than one year and was a candidate for surgical treatment. He was unable to walk up and down steps and had constant and severe pain. After eighteen treatments with magnetic therapy (MT), as described herein, be had very dramatic and near complete resolution of the symptoms. A second and third M.R.I. study to be performed one and six months after the eighteenth treatment is scheduled.

Example 2

Patient #2 had arthritis of the right knee with chronic effusions, cartilaginous disease of the medial and lateral meniscus with chronic pain on ambulation. Following eleven MT treatments, as described herein, complete resolution of his effusion and the pain associated with his arthritis were effected. Blinded Roentgenographic studies have demonstrated the resolution of effusion.

Examples 3 and 4

Patients #3 and #4 had elbow epicondylitis, sub-acute but of more than six months and more than one year duration. One patient had hypothyroidism and the other patient had no underlying cause for the epicondylitis. Both patients responded dramatically after eighteen MT treatments, as described herein, i.e. they were able to resume pre-morbid housekeeping and professional activities fully and without pain or tenderness.

Example 5

Patient #5 had severe flexor tendonitis of several years duration involving the second, third and fourth flexor tendons and osteoarthritis of the P.I.P. joints. The patient had severe and chronic pain, was unable to bold or grasp his golf clubs for several years. He was not able to hold or carry a paper bag of groceries of minimal weight. After eighteen one-half hour sessions with MT, as described herein, this patient had complete resolution of his pain syndrome and stated that he "felt (his) hand actually younger looking" (patient's quote).

Further Examples

Fifty joints were each treated eighteen times with magnetic therapy as described herein. Based on objective and subjective 112 variable parameters, a rating based on merit points was developed which provided an overall "Response" which was summarized by a blinded Chief Rheumatologist (Clinical Investigator). The following lists indicate the placement of all fifty joints in the Actively Treated Group and the Placebo Treated Group. It can be said that the Definite and Improved Groups demonstrated a significant betterment while the Slight and None Groups did not profit from the therapy.

| ACTIVE TREATED GROUP | | PLACEBO TREATED GROUP | |
|---|---|---|---|
| Definite improvement = | 18 | Definite improvement = | 4 |
| Improved = | 2 | Improved = | 2 |
| Slight improvement = | 2 | Slight improvement = | 3 |
| None = | 1 | None = | 15 |
| TOTAL = | 23 | TOTAL = | 24 |

ACTIVE TREATED GROUP PLACEBO TREATED GROUP 50 patients were treated Actively and with Placebo.

47 patients completed the planned study without indicent 1 patient with 2 joints was hospitalized due to pneumonia.

1 patient with 1 joint moved out of state.

Thus, it should be clear from the above examples that the invention herein disclosed has had dramatic results when used in its preferred form. It is envisioned that some changes within the patterns of the invention so far described are possible, the described characteristics being merely preferred.

Proof of the efficacy of the invention is available from more scientific indicies. As is well known, chromatin is the substance of chromosomes, the portion of the cell nucleus which plays a role in cell division. It is subdivided into euchromatin, the active portion, and heterochromatin, the inactive portion.

It has been demonstrated by electonmicroscopy that healthy synovium of patients under 70 years of age usually exhibits greater than 50% euchromatin and less than 50% heterochromatin whereas patients with diseased synovial tissue usually demonstrate less than 50% euchromatin and greater then 50% heterochromatin. Repeated biopsy specimens of synovium in patients with arthritic disease, when examined under electronmicroscopy, demonstrated greater amounts of heterochromatin than euchromatin. These same patients underwent 12 to 18 treatments with magnetic field therapy and were re-biopsied. The relationship of euchromatin to heterochromatin was then noted to be reversed, i.e. The euchromatin was consistently greater than 50% and the heterochromatin was consistently less than 50.

As stated, the invention is susceptible of various changes and is not limited as described in the examples above. The invention may be, therefore, defined as having the scope of the following claim language or reasonable equivalents thereof.

What is claimed is:

1. An apparatus for treating a part of the body with magnetic therapy comprising a horizontal patient-support surface, a pair of spaced parallel tracks at one side and at a level below the support surface, a pair of spaced parallel rails above the tracks, a patient-support web attached to and bridging across the rails, means supporting the patient-support surface, the tracks, and the rails in the above-indicated relationship, a carriage supported by the tracks and anti-friction means on the carriage-engaging the tracks, a toroid having a central opening supported in vertical disposition on the carriage and receiving within its opening the rails and patient-support web, the toroid containing magnetic-field-producing coil means, and means to energize the coil means.

2. The apparatus as claimed in claim 1 wherein the carriage has upward parallel recesses in its bottom surface and the anti-friction means are disposed in the recesses.

3. An apparatus as claimed in claim 1 wherein the tracks, rails and web are of non-ferrous material.

4. Apparatus for treatment of a diseased body organ with magnetic field therapy comprising:

a. a toroidally shaped case containing a series of circularly arranged arcuate segments of wound coil disposed substantially continuously about the toroid, the toroid having a central opening adapted to receive the diseased body organ;

b. a power supply connected to the coil segments and driving the coil segments with a pulsed DC voltage having a rectangular wave form consisting of an abruptly rising and abruptly deteriorating current pulsing at the rate of 1–30 pulse bursts per second and power to energize the coil segments to produce a field of under 20 Gauss in the central opening of the toroid.

5. Apparatus as claimed in claim 4 wherein the diameter of the opening in the toroid is about 5½".

6. Apparatus as claimed in claim 4 wherein the diameter of the opening in the toroid is about 11".

7. Apparatus as claimed in claim 4 wherein the diameter of the opening in the toroid is about 22".

8. Apparatus as claimed in claim 1 wherein the magnetic-field-producing coil means comprises a plurality of spaced coil segments.

9. Apparatus for treating a diseased body organ, the apparatus comprising means for, in the absence of any electrical field, subjecting the body organ to an electromagnetic field of under 20 Gauss, said means including an annular coil means within the opening of which the body organ is placed, a pulsed DC voltage means having a rectangular wave form consisting of an abruptly rising and abruptly deteriorating current pulsing at the rate of 1–30 pulse bursts per second the coil means being driven by said pulsed DC voltage means.

* * * * *